(12) United States Patent  
Attar

(10) Patent No.: US 11,786,224 B2
(45) Date of Patent: *Oct. 17, 2023

(54) BODILY EMISSION ANALYSIS

(71) Applicant: OUTSENSE DIAGNOSTICS LTD., Or Yehuda (IL)

(72) Inventor: Ishay Attar, M.P. Hof Carmel (IL)

(73) Assignee: OUTSENSE DIAGNOSTICS LTD., Or Yehuda (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/412,962

(22) Filed: Aug. 26, 2021

(65) Prior Publication Data
US 2021/0386408 A1 Dec. 16, 2021

Related U.S. Application Data

(63) Continuation of application No. 16/700,423, filed on Dec. 2, 2019, now Pat. No. 11,129,599, which is a (Continued)

(51) Int. Cl.
*A61B 10/00* (2006.01)
*G01N 33/493* (2006.01)
(Continued)

(52) U.S. Cl.
CPC ........ *A61B 10/0038* (2013.01); *A61B 10/007* (2013.01); *G01J 3/10* (2013.01); (Continued)

(58) Field of Classification Search
CPC ........ G01N 21/31; G01N 33/493; G01J 3/42; G01J 3/10; G01J 3/2803; A61B 10/007; (Continued)

(56) References Cited

U.S. PATENT DOCUMENTS 4,636,474 A 1/1987 Ogura et al.
5,277,181 A 1/1994 Mendelson et al.
(Continued)

FOREIGN PATENT DOCUMENTS

EP 1167971 A2 1/2002
EP 3159691 A1 4/2017
(Continued)

OTHER PUBLICATIONS

Examination Report for CA2,977,743 dated Mar. 22, 2022.
(Continued)

*Primary Examiner* — Vu Le
*Assistant Examiner* — Tracy Mangialaschi
(74) *Attorney, Agent, or Firm* — Dorsey & Whitney LLP

(57) ABSTRACT

Apparatus and methods are described for use with a bodily emission of a subject that is disposed within a toilet bowl. While the bodily emission is disposed within the toilet bowl, light is received from the toilet bowl using one or more light sensors. Using a computer processor, intensities of at least two spectral bands that are within a range of 530 nm to 785 nm are determined, by analyzing the received light, and a ratio of the intensities of the two spectral bands is determined. In response thereto, the computer processor determines that there is a presence of blood within the bodily emission. The computer processor generates an output on an output device, at least partially in response thereto. Other applications are also described.

17 Claims, 7 Drawing Sheets

Related U.S. Application Data continuation of application No. 15/553,366, filed as application No. PCT/IL2016/050223 on Feb. 25, 2016, now Pat. No. 10,575,830.

(60) Provisional application No. 62/120,639, filed on Feb. 25, 2015.

(51) Int. Cl.

| | | |
|---|---|---|
| G01N 21/31 | (2006.01) | |
| G01J 3/42 | (2006.01) | |
| G01J 3/10 | (2006.01) | |
| G01J 3/28 | (2006.01) | |
| G06T 7/00 | (2017.01) | |
| E03D 11/13 | (2006.01) | |

(52) U.S. Cl.
CPC ............. *G01J 3/2803* (2013.01); *G01J 3/42* (2013.01); *G01N 21/31* (2013.01); *G01N 33/493* (2013.01); *G06T 7/0014* (2013.01); *A61B 2010/0003* (2013.01); *E03D 11/13* (2013.01); *G06T 2207/10024* (2013.01); *G06T 2207/30004* (2013.01); *G06T 2207/30232* (2013.01)

(58) Field of Classification Search
CPC ........ A61B 10/0038; A61B 2010/0003; G06T 7/0014; G06T 2207/30232; G06T 2207/30004; G06T 2207/10024; E03D 11/13

See application file for complete search history.

(56) References Cited

U.S. PATENT DOCUMENTS

| | | | |
|---|---|---|---|
| 5,730,149 | A | 3/1998 | Nakayama et al. |
| 6,006,119 | A | 12/1999 | Soller et al. |
| 6,572,564 | B2 | 6/2003 | Ito et al. |
| 6,844,195 | B2 | 1/2005 | Craine |
| 7,749,217 | B2 | 7/2010 | Podhajsky |
| 8,750,952 | B2 | 6/2014 | Aalders |
| 8,911,368 | B2 | 12/2014 | Rabinovitz et al. |
| 9,029,161 | B2 | 5/2015 | Aalders et al. |
| 10,575,830 | B2 | 3/2020 | Attar |
| 11,129,599 | B2 | 9/2021 | Attar |
| 11,467,091 | B2 | 10/2022 | Attar et al. |
| 2003/0232446 | A1 | 12/2003 | Scholl et al. |
| 2005/0037505 | A1 | 2/2005 | Samsoondar |
| 2005/0154277 | A1* | 7/2005 | Tang .............. A61B 1/00156 600/407 |
| 2005/0261605 | A1 | 11/2005 | Shemer et al. |
| 2010/0099139 | A1 | 4/2010 | Ben-David et al. |
| 2011/0051125 | A1 | 3/2011 | Kim |
| 2011/0306855 | A1 | 12/2011 | Rabinovitz et al. |
| 2012/0196271 | A1 | 8/2012 | Ingber |
| 2014/0147924 | A1 | 5/2014 | Wheeldon et al. |
| 2015/0359522 | A1* | 12/2015 | Recht .............. G01N 21/6486 600/573 |
| 2016/0000378 | A1 | 1/2016 | Hall et al. |
| 2016/0120449 | A1 | 5/2016 | Chiba |
| 2016/0278705 | A1 | 9/2016 | Han et al. |
| 2017/0303901 | A1 | 10/2017 | Sekine |
| 2017/0307512 | A1 | 10/2017 | Akagawa et al. |
| 2018/0085098 | A1 | 3/2018 | Attar |
| 2018/0303466 | A1 | 10/2018 | Kashyap et al. |
| 2019/0195802 | A1 | 6/2019 | Attar et al. |
| 2020/0100771 | A1 | 4/2020 | Attar |
| 2021/0389250 | A1 | 12/2021 | Attar et al. |

FOREIGN PATENT DOCUMENTS

| | | |
|---|---|---|
| JP | H05126826 A | 5/1993 |
| JP | H07113804 | 5/1995 |
| JP | H0978656 A | 3/1997 |
| JP | 2000241347 A | 9/2000 |
| JP | 2005037278 A | 2/2005 |
| JP | 2005524441 A | 8/2005 |
| JP | 2006189338 A | 7/2006 |
| JP | 2007252805 A | 10/2007 |
| JP | 2012532122 A | 12/2012 |
| JP | 2016004005 A | 1/2016 |
| JP | 2020201279 A | 12/2020 |
| KR | 20170078450 A | 7/2017 |
| WO | 2011123776 A2 | 10/2011 |
| WO | 2013082267 A1 | 6/2013 |
| WO | 2014171018 A1 | 10/2014 |
| WO | 2014192781 A1 | 12/2014 |
| WO | 2015194405 A1 | 12/2015 |
| WO | 2016063547 A1 | 4/2016 |
| WO | 2016135735 A1 | 9/2016 |
| WO | 2018042431 A1 | 3/2018 |
| WO | 2018222939 A1 | 12/2018 |
| WO | 2021205345 A1 | 10/2021 |

OTHER PUBLICATIONS

Office Action for KR 10-2017-7027062 dated Apr. 25, 2022 with English machine translation and partial English translation by associate.
Corrected Notice of Allowance for U.S. Appl. No. 15/553,366 dated Jan. 29, 2020.
Corrected Notice of Allowance for U.S. Appl. No. 15/553,366 dated Nov. 18, 2018.
European Search Report for European Application No. 16754866.8 dated Nov. 15, 2018.
Examination Report for Australian Application No. 2016224850 dated May 3, 2021.
Examination Report for Australian Application No. 2016224850 dated Sep. 11, 2020.
First Action Interview Office Action received for U.S. Appl. No. 16/700,423 dated Feb. 5, 2021.
International Search Report and Written Opinion from International Application No. PCT/IL2016/050223 dated Jun. 7, 2016.
International Search Report and Written Opinion from International Application No. PCT/IL2017/050966 dated Nov. 28, 2017.
Issue Notification for U.S. Appl. No. 15/553,366 dated Dec. 11, 2019.
Non-Final Office Action for U.S. Appl. No. 15/553,366 dated Feb. 11, 2019.
Notice of Allowance for U.S. Appl. No. 15/553,366 dated Aug. 28, 2019.
Notice of Allowance for U.S. Appl. No. 16/700,423 dated May 27, 2021.
Office Action and English Summary for Chinese Application No. 201680015869.0 dated Aug. 16, 2019.
Office Action and English Translation for Japanese Application No. 2017-544028 dated Dec. 3, 2019.
Office Action for Chinese Application No. 201680015869.0 dated Jun. 5, 2020.
Office Action for Japanese Application No. 2019-510400 dated Jul. 7, 2021.
Preinterview First Office Action for U.S. Appl. No. 16/700,423 dated Dec. 24, 2020.
Supplementary Extended European Search Report for Application No. 17845672.9 dated Jul. 17, 2019.
U.S. Appl. No. 15/553,366, filed Aug. 24, 2017.
U.S. Appl. No. 16/325,632, filed Feb. 14, 2019.
U.S. Appl. No. 16/700,423, filed Dec. 2, 2019.
U.S. Appl. No. 62/120,639, filed Feb. 25, 2015.
U.S. Appl. No. 62/381,288, filed Aug. 30, 2016.
Cullen, et al., "Hyperspectral Imaging for Non-Contact Analysis of Forensic Traces", Forensic Science International, Oct. 22, 2012.
Monici, "Natural flourescence of white blood cells: spectroscopic and imaging study", Journal of Photochemistry and photobilology B:Biology 30, 1995, pp. 29-37.

(56) References Cited

OTHER PUBLICATIONS

Russo, et al., "Hemoglobin, Isolation and Chemical Properties", Journal of Chemical Education, vol. 50, No. 5, May 1973, pp. 347-350.
Extended European Search Report for European Patent Application No. 21180648.4 dated Oct. 28, 2021.
International Search Report and Written Opinion from International Application No. PCT/IB2021/052856 dated Sep. 3, 2021.
Invitation to Pay Additional Fees for International Application No. PCT/IB2021/052856 dated Jul. 8, 2021.
Office Action for Japanese Application No. 2020-146892 dated Sep. 15, 2021.
U.S. Appl. No. 17/462,147, filed Aug. 31, 2021.
Corrected Notice of Allowability for U.S. Appl. No. 17/462,147 dated Nov. 17, 2022.
Examination Report for Canadian Application No. 2,977,743 dated Dec. 16, 2022.
Issue Notification for U.S. Appl. No. 16/325,632 dated Sep. 21, 2022.
Issue Notification for U.S. Appl. No. 17/462,147 dated Jan. 4, 2023.
Notice of Allowance for U.S. Appl. No. 17/462,147 dated Sep. 28, 2022.
Notice of Allowance for U.S. Appl. No. 16/325,632 dated Aug. 9, 2022.
Office Action for Japanese Application No. 2022-022279 dated Feb. 3, 2023.
Imai, et al., "The Effective Method of Feces for Occult Blood Test in the Detection of Colorectal Cancer", Second Department of Surgery, Yokohama City University, School of Medicine, 1992, 9 pages.
Office Action for Japanese Application No. 2022-075244 dated Jul. 3, 2023.
Examination Report for European Application No. 21180648.4 dated Jul. 20, 2023.
Notice of Allowance for U.S. Appl. No. 18/085,685 dated Sep. 8, 2023.
Office Action for Korean Application No. 10-2023-7021073 dated Aug. 16, 2023.

* cited by examiner

BODILY EMISSION ANALYSIS

CROSS-REFERENCE TO RELATED APPLICATIONS

The present application is a continuation of U.S. patent application Ser. No. 16/700,423 to Attar filed Dec. 2, 2019 (published as US 2020/0100771), which is a continuation of U.S. patent application Ser. No. 15/553,366 to Attar filed Aug. 24, 2017 (issued as U.S. Pat. No. 10,575,830), which is the U.S. national phase of International application PCT/IL2016/050223 to Attar (published as WO 16/135735), filed Feb. 25, 2016, entitled "Bodily emission analysis," which claims priority from U.S. Provisional Application No. 62/120,639 to Attar, filed Feb. 25, 2015, entitled "Apparatus and method for the remote sensing of blood in an ex-vivo biological sample."

The above-referenced US Provisional application is incorporated herein by reference.

FIELD OF EMBODIMENTS OF THE INVENTION

Some applications of the present invention generally relate to analysis of bodily emissions. Specifically, some applications of the present invention relate to apparatus and methods for detecting blood in bodily emission, such as urine and feces.

BACKGROUND

Colorectal cancer is the development of cancer in portions of the large intestine, such as the colon or rectum. Detection of blood in feces is used as a screening tool for colorectal cancer. However, the blood is often occult blood, i.e., blood that is not visible. The stool guaiac test is one of several methods that detect the presence of blood in feces, even in cases in which the blood is not visible. A fecal sample is placed on a specially prepared type of paper, called guaiac paper, and hydrogen peroxide is applied. In the presence of blood, a blue color appears on the paper. A patient who is suspected of suffering from colorectal cancer will typically be assessed using a colonoscopy, sigmoidoscopy, and/or external imaging techniques, such as CT, PET, and/or MRI.

Bladder cancer is a condition in which cancerous cells multiply within the epithelial lining of the urinary bladder. Detection of blood in urine can be useful in screening for bladder cancer. Techniques for detecting blood include placing a test strip that contains certain chemicals into sample of the urine and detecting a color change of the test strip.

SUMMARY OF EMBODIMENTS

In accordance with some applications of the present invention, a bodily emission of a subject that is disposed within a toilet bowl (such as feces or urine) is analyzed automatically. Typically, while the bodily emission is disposed within the toilet bowl, light (which is reflected from the contents of the toilet bowl) is received from the toilet bowl using one or more light sensors, for example, one or more cameras. Using a computer processor, one or more spectral components within the received light that are indicative of light absorption by a component of erythrocytes are detected, by analyzing the received light (e.g., by performing spectral analysis on the received light). In response thereto, the computer processor determines that there is a presence of blood within the bodily emission. The computer processor typically generates an output on an output device (such as a phone, tablet device, or personal computer), at least partially in response thereto. For some applications, the output device includes an output component (such as a light (e.g., an LED) or a screen) that is built into the device. Typically, subsequent to the subject emitting the bodily emission into the toilet bowl, the above-described steps are performed without requiring any action to be performed by any person. Thus, for example, the subject is not required to add anything to the toilet bowl in order to facilitate the determination of whether there is blood in the emission.

For some applications, the apparatus analyzes and logs the results of multiple bodily emissions of the subject over an extended period of time, e.g., over more than one week, or more than one month. Typically, in this manner, the apparatus is configured to screen for the presence of early stage cancer and/or polyps, which characteristically bleed only intermittently. For some applications, the apparatus compares the amount of blood that is detected in bodily emissions (e.g., feces), over a period of time, to a threshold amount.

There is therefore provided, in accordance with some applications of the present invention, a method for use with a bodily emission of a subject that is disposed within a toilet bowl, the method including:

while the bodily emission is disposed within the toilet bowl, receiving light from the toilet bowl using one or more light sensors;

using a computer processor:
  detecting one or more spectral components within the received light that are indicative of light absorption by a component of erythrocytes, by analyzing the received light;
  in response thereto, determining that there is a presence of blood within the bodily emission; and
  generating an output on an output device, at least partially in response thereto.

In some applications, the bodily emission includes feces, and determining that there is a presence of blood within the bodily emission includes determining that there is a presence of blood within the feces. In some applications, the bodily emission includes urine, and determining that there is a presence of blood within the bodily emission includes determining that there is a presence of blood within the urine.

In some applications, the method further includes logging data regarding blood in a plurality of bodily emissions of the subject, and generating the output includes generating an output in response to the logged data.

In some applications, receiving light from the toilet bowl using one or more light sensors includes receiving one or more images from the toilet bowl using one or more cameras, and detecting one or more spectral components within the received light includes identifying spectral components within respective portions of the bodily emission, by analyzing a plurality of respective pixels within the one or more images on an individual basis.

In some applications, receiving light from the toilet bowl using one or more light sensors includes, subsequent to the subject emitting the bodily emission into the toilet bowl, receiving the light from the toilet bowl using one or more light sensors, without requiring any action to be performed by any person subsequent to the emission.

In some applications, receiving light from the toilet bowl using one or more light sensors includes receiving light from the toilet bowl using a spectrometer. In some applications, receiving light from the toilet bowl using one or more light sensors includes receiving light from the toilet bowl using one or more monochrome cameras. In some applications, receiving light from the toilet bowl using one or more light sensors includes receiving light from the toilet bowl using one or more color cameras. In some applications, receiving light from the toilet bowl using one or more light sensors includes receiving light from the toilet bowl using one or more monochrome cameras, and using one or more color cameras.

In some applications, the method further includes, in response to determining that there is a presence of blood within the bodily emission, requesting an input from the subject that is indicative of a source of the blood.

In some applications, detecting the one or more spectral components within the received light that are indicative of light absorption by a component of erythrocytes includes detecting one or more spectral components within the received light that are indicative of light absorption by a component of erythrocytes, the component being selected from the group consisting of: hemoglobin, oxyhemoglobin, methemoglobin, and heme.

In some applications, the method further includes detecting one or more spectral components within the received light that are indicative of light absorption by a bodily emission selected from the group consisting of: feces and urine.

In some applications, the method further includes illuminating the emission within the toilet bowl, and receiving the light includes receiving reflected light resulting from the illumination. In some applications, illuminating the emission within the toilet bowl includes illuminating the emission within the toilet bowl using white light. In some applications, illuminating the emission within the toilet bowl includes illuminating the emission within the toilet bowl with light at one or more spectral bands.

In some applications, detecting the one or more spectral components includes detecting one or more spectral bands that are centered around a wavelength that is within a range of 530 nm to 785 nm. In some applications, detecting the one or more spectral components includes detecting one or more spectral bands that are centered around an approximate wavelength selected from the group consisting of: 540 nm, 565 nm, and 575 nm. In some applications, detecting the one or more spectral bands includes detecting one or more spectral bands having a bandwidth of less than 40 nm.

In some applications, detecting the one or more spectral bands includes detecting at least two of the spectral bands, the method further including determining a relationship between intensities of respective spectral bands of the at least two spectral bands, and determining that there is a presence of blood within the bodily emission includes determining that there is a presence of blood within the bodily emission at least partially based upon the determined relationship.

In some applications, determining the relationship between intensities of respective spectral bands of the at least two spectral bands includes:
 determining a first ratio between an intensity of a band that is centered around approximately 565 nm to an intensity of a band that is centered around approximately 575 nm; and
 determining a second ratio between an intensity of the band that is centered around approximately 565 nm to an intensity of a band that is centered around approximately 540 nm.

In some applications, receiving light from the toilet bowl using one or more light sensors includes receiving light from the toilet bowl using a multispectral camera. In some applications, analyzing the received light includes generating a hypercube of data that contains two spatial dimensions and one wavelength dimension.

There is further provided, in accordance with some applications of the present invention, apparatus for use with a bodily emission of a subject that is disposed within a toilet bowl, and an output device, the apparatus including:
 one or more light sensors that are configured to receive light from the toilet bowl, while the bodily emission is disposed within the toilet bowl; and
 a computer processor configured to:
  detect one or more spectral components within the received light that indicate light absorption by a component of erythrocytes, by analyzing the received light;
  in response thereto, determining that there is a presence of blood within the bodily emission; and
  generating an output on the output device, at least partially in response thereto.

In some applications, the bodily emission includes feces, and the computer processor is configured to determine that there is a presence of blood within the bodily emission by determining that there is a presence of blood within the feces. In some applications, the bodily emission includes urine, and the computer processor is configured to determine that there is a presence of blood within the bodily emission by determining that there is a presence of blood within the urine.

In some applications, the computer processor is configured to log data regarding blood in a plurality of bodily emissions of the subject, and to generate the output in response to the logged data.

In some applications, the one or more light sensors include one or more cameras configured to acquire one or more images of the bodily emission, and the computer processor is configured to detect the one or more spectral components within the received light by identifying spectral components within respective portions of the bodily emission, by analyzing a plurality of respective pixels within the one or more images on an individual basis.

In some applications, subsequent to the subject emitting the bodily emission into the toilet bowl, the one or more light sensors are configured to receive the light from the toilet bowl, without requiring any action to be performed by any person subsequent to the emission.

In some applications, the one or more light sensors include a spectrometer. In some applications, the one or more light sensors include one or more monochrome cameras.

In some applications, the one or more light sensors include one or more color cameras. In some applications, the one or more light sensors include one or more color cameras and one or more monochrome cameras.

In some applications, in response to determining that there is a presence of blood within the bodily emission, the computer processor is configured to request an input from the subject that is indicative of a source of the blood.

In some applications, the computer processor is configured to detect one or more spectral components within the received light that indicate light absorption by a component of erythrocytes, by detecting one or more spectral components within the received light that are indicative of light absorption by a component of erythrocytes, the component being selected from the group consisting of: hemoglobin, oxyhemoglobin, methemoglobin, and heme.

In some applications, the computer processor is further configured to detect one or more spectral components within the received light that are indicative of light absorption by a bodily emission selected from the group consisting of: feces and urine.

In some applications, the apparatus further includes a light source configured to illuminate the emission within the toilet bowl, the one or more light sensors are configured to receive reflected light resulting from the illumination. In some applications, the light source is configured to illuminate the emission within the toilet bowl using white light.

In some applications, the light source is configured to illuminate the emission within the toilet bowl using light at one or more spectral bands.

In some applications, the computer processor is configured to detect the one or more spectral components by detecting one or more spectral bands that are centered around a wavelength that is within a range of 530 nm to 785 nm. In some applications, the computer processor is configured to detect the one or more spectral components by detecting one or more spectral bands that are centered around an approximate wavelength selected from the group consisting of: 540 nm, 565 nm, and 575 nm. In some applications, the computer processor is configured to detect the one or more spectral components by detecting one or more spectral bands having a bandwidth of less than 40 nm.

In some applications, the computer processor is configured to:
 detect at least two of the spectral bands,
 determine a relationship between intensities of respective spectral bands of the at least two spectral bands, and
 determine that there is a presence of blood within the bodily emission by determining that there is a presence of blood within the bodily emission at least partially based upon the determined relationship.

In some applications, the computer processor is configured to determine the relationship between intensities of respective spectral bands of the at least two spectral bands by:
 determining a first ratio between an intensity of a band that is centered around approximately 565 nm to an intensity of a band that is centered around approximately 575 nm; and
 determining a second ratio between an intensity of the band that is centered around approximately 565 nm to an intensity of a band that is centered around approximately 540 nm.

In some applications, the one or more light sensors include a multispectral camera. In some applications, the computer processor is configured to analyze the received light by generating a hypercube of data that contains two spatial dimensions and one wavelength dimension.

There is further provided, in accordance with some applications of the present invention, a method including:
 subsequent to a subject emitting a bodily emission into a toilet bowl, and without requiring any action to be performed by any person subsequent to the emission:
  receiving light from the toilet bowl, using one or more light sensors; and
  using a computer processor:
   analyzing the received light;
   in response thereto, determining that there is a presence of blood within the bodily emission; and
   generating an output on an output device, at least partially in response thereto.

In some applications, the bodily emission includes feces, and determining that there is a presence of blood within the bodily emission includes determining that there is a presence of blood within the feces. In some applications, the bodily emission includes urine, and determining that there is a presence of blood within the bodily emission includes determining that there is a presence of blood within the urine.

In some applications, the method further includes logging data regarding blood in a plurality of bodily emissions of the subject, and generating the output includes generating an output in response to the logged data.

In some applications, receiving light from the toilet bowl using one or more light sensors includes receiving one or more images from the toilet bowl using one or more cameras, and analyzing the received light includes detecting one or more spectral components within the received light by identifying spectral components within respective portions of the bodily emission, by analyzing a plurality of respective pixels within the one or more images on an individual basis.

In some applications, receiving light from the toilet bowl using one or more light sensors includes receiving light from the toilet bowl using a spectrometer. In some applications, receiving light from the toilet bowl using one or more light sensors includes receiving light from the toilet bowl using one or more monochrome cameras. In some applications, receiving light from the toilet bowl using one or more light sensors includes receiving light from the toilet bowl using one or more color cameras. In some applications, receiving light from the toilet bowl using one or more light sensors includes receiving light from the toilet bowl using one or more monochrome cameras, and using one or more color cameras.

In some applications, the method further includes, in response to determining that there is a presence of blood within the bodily emission, requesting an input from the subject that is indicative of a source of the blood.

In some applications, the method further includes illuminating the emission within the toilet bowl, receiving the light includes receiving reflected light resulting from the illuminating. In some applications, illuminating the emission within the toilet bowl includes illuminating the emission within the toilet bowl using white light. In some applications, illuminating the emission within the toilet bowl includes illuminating the emission within the toilet bowl with light at one or more spectral bands.

In some applications, analyzing the received light includes detecting one or more spectral components within the received light that indicate light absorption by a component of erythrocytes. In some applications, detecting the one or more spectral components within the received light that are indicative of light absorption by a component of erythrocytes includes detecting one or more spectral components within the received light that are indicative of light absorption by a component of erythrocytes, the component being selected from the group consisting of: hemoglobin, oxyhemoglobin, methemoglobin, and heme.

In some applications, the method further includes detecting one or more spectral components within the received light that are indicative of light absorption by a bodily emission selected from the group consisting of: feces and urine.

In some applications, detecting the one or more spectral components includes detecting one or more spectral bands that are centered around a wavelength that is within a range of 530 nm to 785 nm. In some applications, detecting the one or more spectral components includes detecting one or more spectral bands that are centered around an approximate wavelength selected from the group consisting of: 540 nm, 565 nm, and 575 nm. In some applications, detecting the one or more spectral bands includes detecting one or more spectral bands having a bandwidth of less than 40 nm.

In some applications, detecting the one or more spectral bands includes detecting at least two of the spectral bands, the method further including determining a relationship between intensities of respective spectral bands of the at least two spectral bands, and determining that there is a presence of blood within the bodily emission includes determining that there is a presence of blood within the bodily emission at least partially based upon the determined relationship.

In some applications, determining the relationship between intensities of respective spectral bands of the at least two spectral bands includes:

determining a first ratio between an intensity of a band that is centered around approximately 565 nm to an intensity of a band that is centered around approximately 575 nm; and determining a second ratio between an intensity of the band that is centered around approximately 565 nm to an intensity of a band that is centered around approximately 540 nm.

In some applications, receiving light from the toilet bowl using one or more light sensors includes receiving light from the toilet bowl using a multispectral camera. In some applications, analyzing the received light includes generating a hypercube of data that contains two spatial dimensions and one wavelength dimension.

There is further provided, in accordance with some applications of the present invention, apparatus for use with a bodily emission of a subject that is disposed within a toilet bowl, and an output device, the apparatus including:

one or more cameras that are configured to receive one or more images from the toilet bowl, while the bodily emission is disposed within the toilet bowl; and a computer processor configured to:
 detect spectral components within respective portions of the bodily emission, by analyzing a plurality of respective pixels within the one or more images on an individual basis;
 in response thereto, determining that there is a presence of blood within the bodily emission; and
 generating an output on the output device, at least partially in response thereto.

In some applications, the bodily emission includes feces, and the computer processor is configured to determine that there is a presence of blood within the bodily emission by determining that there is a presence of blood within the feces. In some applications, the bodily emission includes urine, and the computer processor is configured to determine that there is a presence of blood within the bodily emission by determining that there is a presence of blood within the urine.

In some applications, the computer processor is configured to log data regarding blood in a plurality of bodily emissions of the subject, and to generate the output in response to the logged data.

In some applications, subsequent to the subject emitting the bodily emission into the toilet bowl, the one or more light sensors are configured to receive the light from the toilet bowl, without requiring any action to be performed by any person subsequent to the emission.

In some applications, the one or more cameras include one or more monochrome cameras. In some applications, the one or more cameras include one or more color cameras. In some applications, the one or more cameras include one or more color cameras and one or more monochrome cameras.

In some applications, in response to determining that there is a presence of blood within the bodily emission, the computer processor is configured to request an input from the subject that is indicative of a source of the blood.

In some applications, the apparatus further includes a light source configured to illuminate the emission within the toilet bowl, the one or more cameras are configured to receive reflected light resulting from the illumination. In some applications, the light source is configured to illuminate the emission within the toilet bowl using white light. In some applications, the light source is configured to illuminate the emission within the toilet bowl using light at one or more spectral bands.

In some applications, the computer processor is configured to detect spectral components within respective portions of the bodily emission by detecting one or more spectral components of respective pixels that indicate light absorption by a component of erythrocytes. In some applications, the computer processor is configured to detect one or more spectral components of the respective pixels that indicate light absorption by a component of erythrocytes, by detecting one or more spectral components of the respective pixels that are indicative of light absorption by a component of erythrocytes, the component being selected from the group consisting of: hemoglobin, oxyhemoglobin, methemoglobin, and heme.

In some applications, the computer processor is further configured to detect one or more spectral components of the respective pixels that are indicative of light absorption by a bodily emission selected from the group consisting of: feces and urine.

In some applications, the computer processor is configured to detect the one or more spectral components by detecting one or more spectral bands that are centered around a wavelength that is within a range of 530 nm to 785 nm. In some applications, the computer processor is configured to detect the one or more spectral components by detecting one or more spectral bands that are centered around an approximate wavelength selected from the group consisting of: 540 nm, 565 nm, and 575 nm. In some applications, the computer processor is configured to detect the one or more spectral components by detecting one or more spectral bands having a bandwidth of less than 40 nm.

In some applications, the computer processor is configured to:
 detect at least two of the spectral bands,
 determine a relationship between intensities of respective spectral bands of the at least two spectral bands, and
 determine that there is a presence of blood within the bodily emission by determining that there is a presence of blood within the bodily emission at least partially based upon the determined relationship.

In some applications, the computer processor is configured to determine the relationship between intensities of respective spectral bands of the at least two spectral bands by:

determining a first ratio between an intensity of a band that is centered around approximately 565 nm to an intensity of a band that is centered around approximately 575 nm; and determining a second ratio between an intensity of the band that is centered around approximately 565 nm to an intensity of a band that is centered around approximately 540 nm.

In some applications, the one or more cameras include a multispectral camera. In some applications, the computer processor is configured to analyze the plurality of respective pixels within the one or more images on an individual basis by generating a hypercube of data that contains two spatial dimensions and one wavelength dimension.

There is further provided, in accordance with some applications of the present invention, a method for use with a bodily emission of a subject that is disposed within a toilet bowl, the method including:

while the bodily emission is disposed within the toilet bowl, receiving one or more images from the toilet bowl using one or more cameras;
using a computer processor:
detecting spectral components within respective portions of the bodily emission, by analyzing a plurality of respective pixels within the one or more images on an individual basis;
in response thereto, determining that there is a presence of blood within the bodily emission; and
generating an output on an output device, at least partially in response thereto.

There is further provided, in accordance with some applications of the present invention, a method including:

subsequent to a subject emitting a bodily emission into a toilet bowl, and without requiring any action to be performed by any person subsequent to the emission:
receiving light from the toilet bowl, using one or more light sensors; and
storing data relating to the received light in a memory.

The present invention will be more fully understood from the following detailed description of embodiments thereof, taken together with the drawings, in which:

DETAILED DESCRIPTION OF EMBODIMENTS

Figure 1:
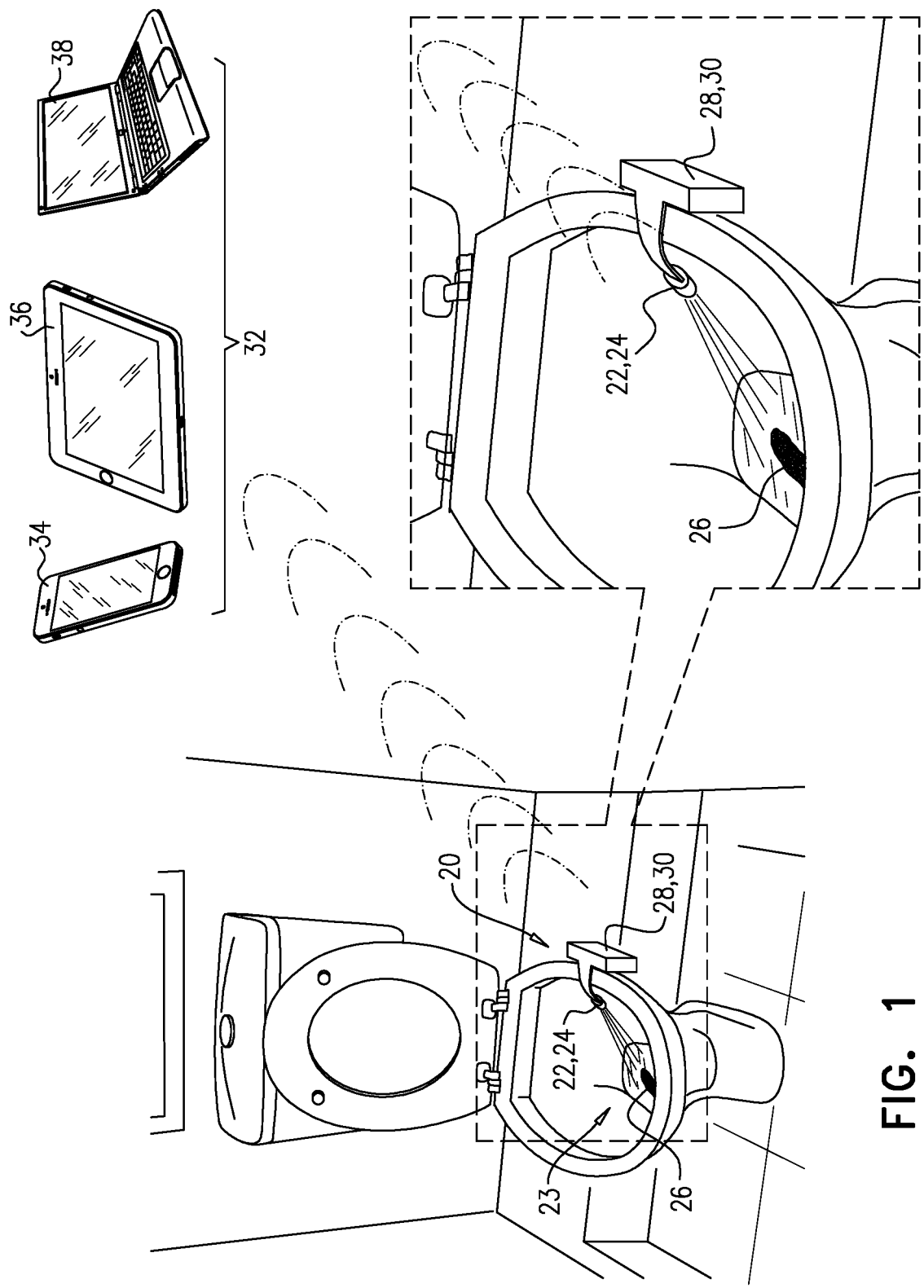
FIG. 1 is a schematic illustration of apparatus for analyzing a bodily emission, in accordance with some applications of the present invention.

Reference is now made to FIG. 1, which is a schematic illustration of apparatus 20 for analyzing a bodily emission, in accordance with some applications of the present invention. As shown, apparatus 20 typically includes a sensor module 22, which is placed inside a toilet bowl 23. The sensor module includes an imaging component 24, which in turn includes one or more light sensors that are configured to receive light from bodily emissions (typically, urine or feces 26) that were emitted by the subject and are disposed inside the toilet bowl. For example, the light sensors may include a spectrometer, or may include one or more cameras, as described in further detail hereinbelow. A computer processor analyzes the received light, and determines whether there is a presence of blood inside the bodily emission. Typically, the computer processor detects one or more spectral components within the received light that are indicative of light absorption by a component of erythrocytes, by analyzing the received light (e.g., by performing spectral analysis on the received light). (Such spectral components may be referred to herein as a blood signature, since certain combinations of such components, as described herein, are indicative of the presence of blood.) Further typically, the steps of receiving light, analyzing the received light, and determining whether there is a presence of blood inside the bodily emission are performed without requiring any action to be performed by any person (e.g., the user, a caregiver, or a healthcare professional) subsequent to the subject emitting the bodily emission into the toilet bowl.

For some applications, apparatus 20 includes a power source 28 (e.g., a battery pack), that is disposed outside the toilet bowl inside a housing 30, as shown in FIG. 1. Alternatively or additionally, the sensor module is connected to mains electricity (not shown). Typically, the power source and sensor module 22 are connected wiredly (as shown), or wirelessly (not shown). In accordance with respective applications, the computer processor that performs the above described analysis is disposed inside the toilet bowel (e.g., inside the same housing as the sensor module), inside housing 30, or remotely. For example, as shown, the sensor module may communicate wirelessly with a user interface device 32 that includes a computer processor. Such a user interface device may include, but is not limited to, a phone 34, a tablet computer 36, a laptop computer 38, or a different sort of personal computing device. The user interface device typically acts as both an input device and an output device, via which the user interacts with sensor module 22. The sensor module may transmit data to the user interface device and the user interface device computer processor may run a program that is configured to analyze the light received by the imaging module and to thereby detect whether there is a presence of blood inside the subject's bodily emission.

For some applications, sensor module 22 and/or the user interface device communicates with a remote server. For example, the apparatus may communicate with a physician or an insurance company over a communication network without intervention from the patient. The physician or the insurance company may evaluate the results and determine whether further testing or intervention is appropriate for the patient. For some applications, data relating to the received light are stored in a memory (such as memory 46 described hereinbelow). For example, the memory may be disposed inside the toilet bowl (e.g., inside the sensor unit), inside housing 30, or remotely. Periodically, the subject may submit the stored data to a facility, such as a healthcare facility (e.g., a physician's office, or a pharmacy) or an insurance company, and a computer processor at the facility may then perform the above-described analysis on a batch of data relating to a plurality of bodily emissions of the subject that were acquired over a period of time.

It is noted that the apparatus and methods described herein include a screening test in which the subject is not required to physically touch the bodily emission. Furthermore, the subject is typically only required to touch any portion of the dedicated sensing apparatus periodically, for example, in order to install the device, or to change the device batteries. (It is noted that the subject may handle the user interface device, but this is typically a device (such as a phone) that subject handles even when not using the sensing apparatus.) Further typically, the apparatus and methods described herein do not require adding anything to the toilet bowl subsequent to the subject emitting a bodily emission into the toilet bowl, in order to facilitate the spectral analysis of the emission, and/or a determination that the emission contains blood. For some applications, the subject is not required to perform any action after installation of the apparatus in the toilet bowl. The testing is automatic and handled by the apparatus, and monitoring of the subject's emissions is seamless to the subject and does not require compliance by the subject, so long no abnormality is detected.

Typically, subsequent to the subject emitting a bodily emission into the toilet bowl, the bodily emission is imaged by receiving reflected light from the toilet bowl, without requiring any action to be performed by any person subsequent to the emission. Further typically, the computer processor (a) analyzes (e.g., spectrally analyzes) the received light, (b) in response thereto, determines whether that there is a presence of blood within the bodily emission, and (c) generates an output at least partially in response thereto, all without requiring any action to be performed by any person subsequent to the emission. It is noted that for some applications, an input is requested from the subject, via the user interface device, if an indication of the presence of blood in the bodily emission is detected, as described in further detail hereinbelow. However, even for such applications, it is determined that there is a presence of blood based upon the automatic spectral analysis, and the user input is used in order to determine the source of the blood, and/or to determine whether or not the source of the blood is a cause for concern.

For some applications, for each emission of the subject, in the case of positive signal, the apparatus reports the finding to the patient via an output device, e.g., via user interface device 32. For some applications, the output device includes an output component (such as a light (e.g., an LED) or a screen) that is built into apparatus 20. For some applications, if the analysis of the bodily emission indicates that there is blood present inside the emission, the computer processor drives the user interface to request an input from the subject, by asking the user some verification questions. For example, the user interface device may ask the user "Did you eat red meat in the 24 hours prior to your recent stool emission?" since red meat consumption may cause a false positive due to the meat containing blood. Alternatively or additionally, the user interface device may ask the user "Have you used aspirin or other non-steroidal anti-inflammatory drugs?" since the intake of such drugs has been shown to cause bleeding in the stomach or gastrointestinal tract of susceptible individuals. For some applications, the data are analyzed locally but the results are transmitted to the healthcare provider or to insurance carrier over a network connection.

For some applications, the apparatus monitors bodily emissions of the subject over an extended period of time, e.g., over more than one week, or more than one month. Typically, in this manner, the apparatus is configured to screen for the presence of malignancies and/or polyps, which characteristically bleed only intermittently. For some applications, the apparatus compares the amount of blood that is detected in bodily emissions (e.g., feces), over a period of time, to a threshold amount. It is known that there is a level of normal, physiologic, non-pathogenic gastrointestinal bleeding, which has been estimated as averaging less than 2 ml/day. Intestinal bleeding that is greater than 2 ml/day is considered abnormal. (It is noted that the precise amount that is considered abnormal may differ for each person, depending, for example, on age and sex. Thus, for example, for mature women, normal blood concentration in stool may be considered to be below 64 microgram/gram, whereas for mature males anything above 20 microgram/gram may be considered abnormal.) Therefore, for some applications, the threshold is calibrated to enhance specificity of the sensing, such that alerts will not be generated if the level of bleeding is consistent with normal, physiologic, non-pathogenic gastro-intestinal bleeding, but will generate an alert, if, for example, the level of bleeding is indicative of the presence of cancer and/or polyps.

For some applications, the computer processor which analyzes the received light utilizes machine learning techniques, such as anomaly detection and/or outlier detection. For example, the computer processor may be configured to perform individualized anomaly detection or outlier detection that learns the patterns of output signals from each subject and detects abnormal changes in the characteristic blood signature of the subject. As described hereinabove, for some applications, the computer processor that performs the analysis is remote from and/or separate from the sensor module. For some applications, the sensor module is disposable, but even after disposal of the sensor module the computer processor has access to historic data relating to the subject, such that the historic data can be utilized in the machine learning techniques.

Figure 2:
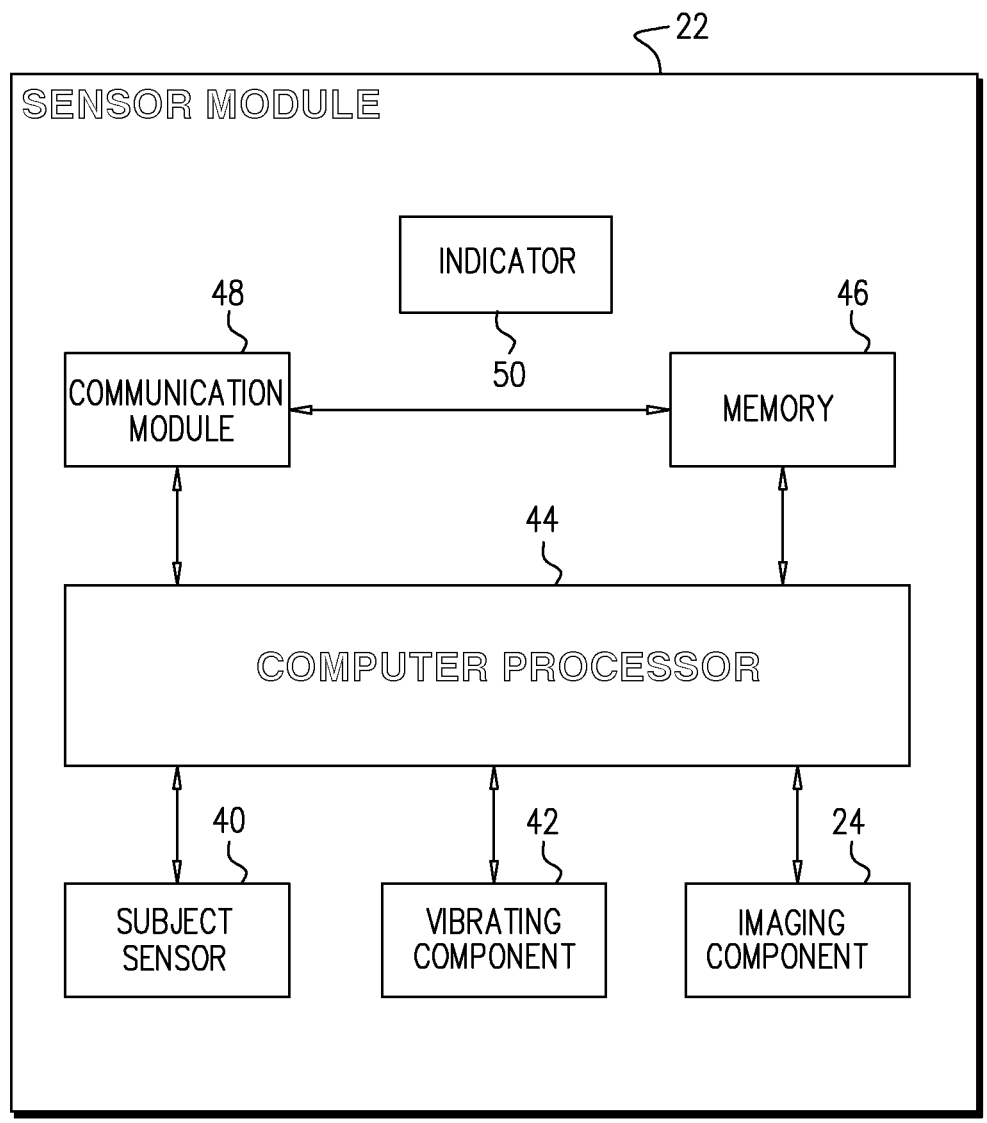
FIG. 2 is a block diagram that schematically illustrates components of a sensor module, in accordance with some applications of the present invention.

Reference is now made to FIG. 2, which is a block diagram that schematically illustrates components of sensor module 22, in accordance with some applications of the present invention. As described hereinabove, sensor module is typically disposed inside a toilet bowl. Further typically, the sensor module includes an imaging component, which in turn includes one or more light sensors that are configured to receive light from bodily emissions that were emitted by the subject and are disposed inside the toilet bowl. The imaging component is described in further detail hereinbelow, with reference to FIGS. 3A-B. Typically, the sensor module is housed in a water-resistant housing. Further typically, the face of the sensor module underneath which the imaging component is mounted is covered with a transparent, water-resistant cover. It is noted that FIG. 1 shows the sensor module disposed above the water level of the water within the toilet bowl. However, for some applications, at least a portion of the sensor module (e.g., the entire sensor module) is submerged within the water in the toilet bowl.

For some applications, the sensor module includes a subject sensor 40. The subject sensor is configured to detect when a subject is on or in the vicinity of the toilet, and/or if the subject has defecated and/or urinated into the toilet bowl. For example, the subject sensor may include a motion sensor, configured to sense the motion of feces, urine, the subject, or the water in the toilet bowl. Alternatively or additionally, the subject sensor may include a light sensor configured to detect when the light in the bathroom is switched on, or when the subject sits on the toilet. For some applications, the light sensors that are used for detecting light from the bodily emission are also used for the aforementioned function. For some such applications, the sensor module is configured to be in standby mode most of the time (such that the sensor module uses a reduced amount of power). The sensor module is switched on in response to detecting that the subject is on or in the vicinity of the toilet, and/or that the subject has defecated and/or urinated into the toilet bowl. Typically, the imaging component of the sensor module acquires images in response to detecting that the subject is on or in the vicinity of the toilet, and/or that the subject has defecated and/or urinated into the toilet bowl. For some applications, the subject switches on the sensor module manually.

For some applications, the sensor module includes a vibrating component 42 that is typically configured to vibrate feces that is inside the toilet bowl. The vibrating element may include an ultrasonic vibrator, a mechanical element that is moved by a motor, and/or a pump configured to emit jets of water. The vibrating element is typically configured to break feces into smaller pieces such that blood that is disposed inside the piece of feces becomes visible to the imaging component. It is noted that, for some applications, the vibrating component is disposed in the toilet bowl separately from the sensor module. For some applications, a vibrating component is not used, but apparatus 20 is able to determine whether there is blood present in feces to a sufficient level of specificity, due to the feces breaking upon falling into the toilet bowl and impacting the toilet bowl.

Typically, the sensor module includes a computer processor 44, a memory 46, and a communication module 48. Computer processor 44 is configured to drive the imaging component to perform the functions described herein. For some applications, the computer processor is further configured to perform the analysis functions described herein. For such applications, computer processor 44 typically communicates the results of the analysis (e.g., a positive detection of blood in feces) to a remote device, such as user interface device 32 (FIG. 1), via communication module 48. Alternatively, as described hereinabove, the analysis of the received light may be performed by a remote computer processor, e.g., a computer processor that is part of the user interface device. For such applications, computer processor 44 typically communicates raw imaging data, and/or light signals to the remote computer processor, via communication module 48. For some applications computer processor stores data in memory 46. The data may include raw data, which may subsequently be retrieved and analyzed, and/or the results of the spectral analysis of the light received by the imaging component. Memory 46 may include a memory card, such as an SD card that can be physically removed. Communication module is typically configured to communicate with external devices (e.g., user interface device 32) using known protocols, such as Wifi, Bluetooth®, ZigBee®, or any near field communication (NFC) protocol.

For some applications, sensor module 22 includes an indicator 50, e.g., a visual indicator (such as an LED light), or an audio indicator (for example, a speaker that is configured to emit a beep), the indicator being configured to indicate to the subject when a sample has been successfully imaged, and/or when data has been successfully transmitted to a remote device, such as user interface device 32. It is noted that, although not shown, the indicator typically interacts with other components of the sensor module such as the computer processor and/or the communication module.

Figure 3B:
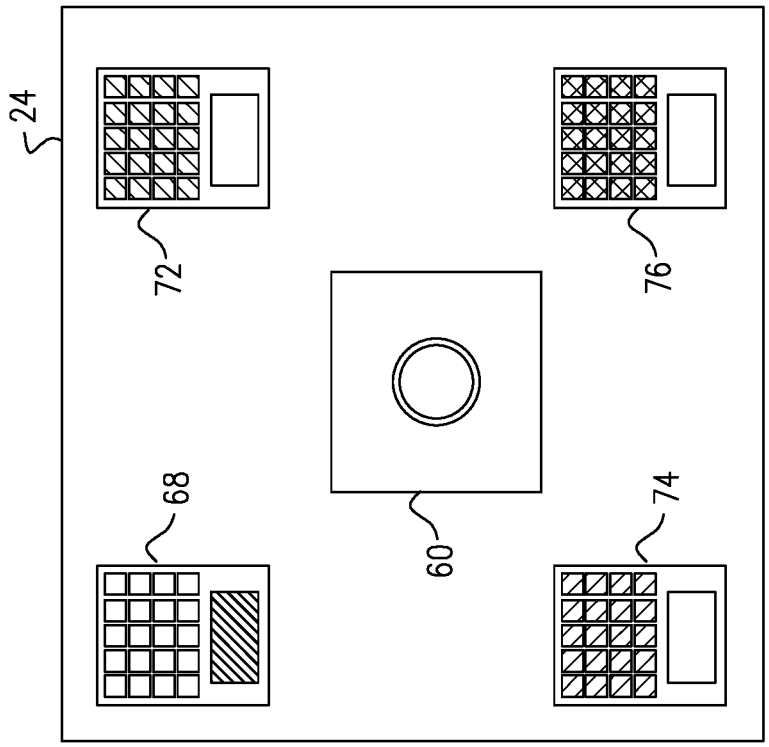
FIG. 3A-B are schematic illustrations of components of an imaging component of the sensor module, in accordance with respective applications of the present invention.
Figure 3A:
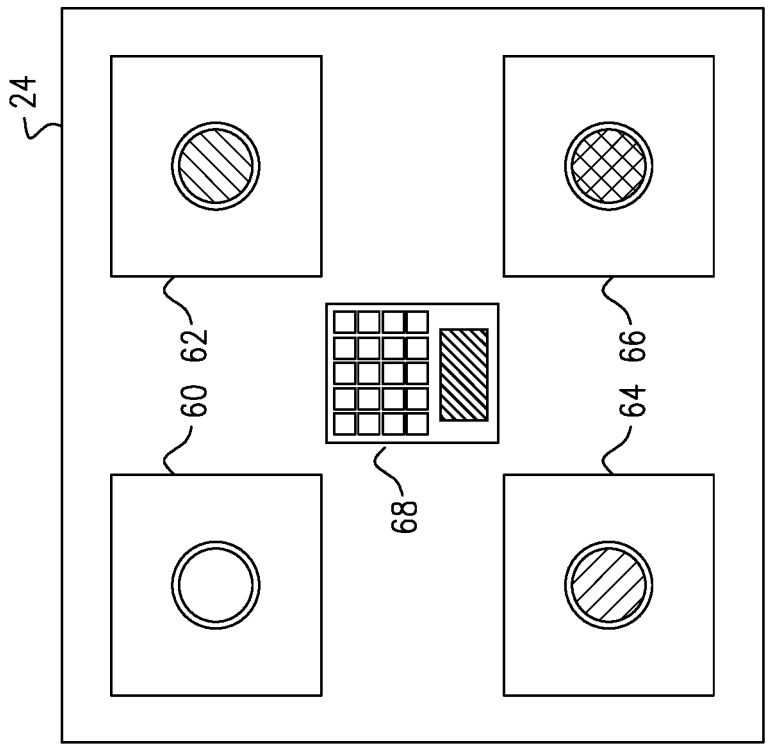

Reference is now made to FIG. 3A-B are schematic illustrations of components of imaging component 24, in accordance with respective applications of the present invention. Imaging component 24 is typically disposed on a face of sensor module 22 that faces toward the water in the toilet bowl. FIGS. 3A-B are schematic illustrations of the aforementioned face of the sensor module.

As described in further detail hereinbelow, typically in order to detect a blood signature within a bodily emission, particular spectral bands within light that is reflected from the bodily emission are detected. Typically, the spectral bands are centered around a wavelength that is in the range of 530 nm to 785 nm. Further typically, two or more spectral bands are detected that are centered around approximately 540 nm, 565 nm, and 575 nm. The widths of the spectral bands are typically greater than 3 nm (e.g., greater than 5 nm, or greater than 8 nm), and/or less than 40 nm (e.g., less than 20 nm, or 12 nm), e.g., between 3 and 40 nm, between 5 and 20 nm or between 8 and 12 nm. A spectral band that is described herein as being centered around approximately a given spectral value should be interpreted as including a spectral band centered around the given value plus/minus 5 nm.

Referring to FIG. 3A, for some applications, imaging component 24 of sensor module 22 includes a light source 68 (e.g., an LED light emitter, or a different type of light) that emits white light. In addition, the imaging module includes two or more cameras, which act as light sensors. The two or more cameras may include a color camera 60, and/or a monochrome camera that includes a filter such as to detect a first one of the above-described spectral bands (camera 62), a second one of the above-described spectral bands (camera 64), and/or a third one of the above-described spectral bands (camera 66). The cameras act as light sensors of apparatus 20, and the light source acts to illuminate the toilet bowl and the bodily emission. For some applications, all four cameras are used in the imaging component.

For some applications, the computer processor of apparatus 20 is configured to identify spectral components within respective portions of the bodily emission, by analyzing respective pixels within the images acquired by the cameras, on an individual basis. In order to identify the spectral components of a given portion of the bodily emission, the computer processor determines a correspondence between pixels of images that were acquired by respective cameras. Typically, irrespective of how many cameras are used, all of the cameras are disposed in close proximity to one another, e.g., such that all of the cameras are disposed within an area of less than 10 square centimeters (e.g., an area of less than 5 square centimeters, or an area of less than 1 square centimeter). For some applications, using cameras that are disposed in close proximity to one another facilitates determining the correspondence between pixels of images that were acquired by respective cameras.

Referring to FIG. 3B, for some applications, imaging component 24 of sensor module 22 includes color camera 60, and includes two or more a light sources (e.g., LED lights or other types of lights) that emit light at respective spectral bands. The two or more light sources typically include light source 68 (which as described with reference to FIG. 3A is configured to emit white light) and/or light sources that are configured to emit light at a first one of the above-described spectral bands (light source 72), a second one of the above-described spectral bands (light source 74), and/or a third one of the above-described spectral bands (light source 76). For some applications, narrowband filters are mounted upon one or more of the light sources. The camera acts as a light sensor of apparatus 20, and the light sources act to illuminate the toilet bowl and the bodily emission. For some applications, all four light sources are used in the imaging component.

It is noted that for some applications, the imaging component does not include a light source, and the light sensors of the imaging component (e.g., the cameras) rely upon ambient light. Alternatively, the light source and the light sensors of the imaging component may be disposed on different sides of the toilet bowl from one another. For some applications, rather than using one or more cameras, which are configured to detect light on a pixel-by-pixel basis, a spectrometer is used to detect the overall spectrum of light that is reflected from the bodily emission, and to analyze the reflected light.

For some applications, color camera 60 is a multispectral camera or a hyperspectral camera. For example, a hyperspectral camera may be used to acquire images of a bodily emission, and the computer processor may analyze the data by generating a hypercube of data that contains two spatial dimensions and one wavelength dimension. The computer processor may determine whether or not there is blood in the bodily emission, by analyzing the hypercube.

It is further noted that the particular arrangements of light sources and light sensors shown in FIGS. 3A-B are examples, and the scope of the present invention includes using alternative or additional arrangements of light sources and/or light detectors. For example, more or fewer than four light sources and/or light sensors may be used. Similarly, the light sources and/or light sensors may be arranged in a different configuration to those shown in FIGS. 3A-B. The scope of the present invention includes using any combination of light sensors and light sources, arranged in any configuration that would facilitate measurements as described herein being performed.

Typically, the light sensors of imaging component 24 of the sensor module 22 acquire images in response to detecting that the subject is on or in the vicinity of the toilet, and/or that the subject has defecated and/or urinated into the toilet bowl, as described hereinabove. For some applications, during the acquisitions of images by camera(s) 60, 62, 64, and/or 66, bursts of images are acquired at given time intervals. For example, a burst may be acquired once every 3 seconds, every 5 second, or every 10 seconds. Each burst of images typically contains between 1 and 8 images, e.g., between 3 and 5 images. Typically, all of the images that are acquired of a given emission are acquired within a total time that is less than 20 seconds, such that there is no substantial movement of the bodily emission between the acquisitions of respective images within each burst. For some applications, the maximum exposure time per image frame is typically 10 ms. Alternatively, the exposure time per image frame may be more than 10 ms, e.g., more than 35 ms.

The apparatus and methods described herein utilize the light reflected back from erythrocytes and collected by light sensors. In some embodiments, this light can be reflected from the ambient light source and in other embodiments a light source is an integral part of the system. In some embodiments, such a light source can be an LED of one or several wavelengths, or a broadband light source with a bandpass filter. As described hereinabove, erythrocytes have a distinct spectral signature, which is reflected from the tested medium and can be detected by light sensors, the signature being referred to herein as the blood signature.

For some applications, the sensor module detects a presence of blood in the bodily emission in response to detecting that the value returned by a mathematical function on the absorption of two or more wavelengths or weighted functions of wavelengths return a certain value. As described hereinabove, for some applications, the sensor module transmits the output of the light sensors to user interface device 32 (FIG. 1) and software that is run by a computer processor on the device performs the analysis.

In general, apparatus 20 typically includes illumination source(s) (i.e., light source(s)) for irradiating biological fluids that are excreted from patient and pass in the toilet bowl water. For some applications, radiation (e.g., radiation in the visible light range) is emitted at various wavelengths of interest, to evaluate the optical signature of the specimen.

A light detector is positioned with respect to the light source(s) on the opposite side, the same side, or anywhere else in the toilet bowl. For example, the light detectors may face the light source(s) such as to detect light from the light source(s) that passes through the bodily emission, or through water that is in contact with the emission. It is noted that although some applications of the present invention relate to using the detection of radiation in the visible light range to perform the techniques described herein, the scope of the present invention includes using radiation at any spectral band to perform techniques described here, mutatis mutandis.

For some applications, a white light broadband illumination source is used (e.g., white light source 68), and the light detector may comprise at least two light detectors (e.g., two or more of cameras 60, 62, 64, and 66). Each light detector may comprise a different filter for collecting light at a different wavelength, after passing through the biological fluids. The filters may be narrow band filters, interference filters, absorbing filters, or diffractive optical element (DOE) filters.

Figure 4:
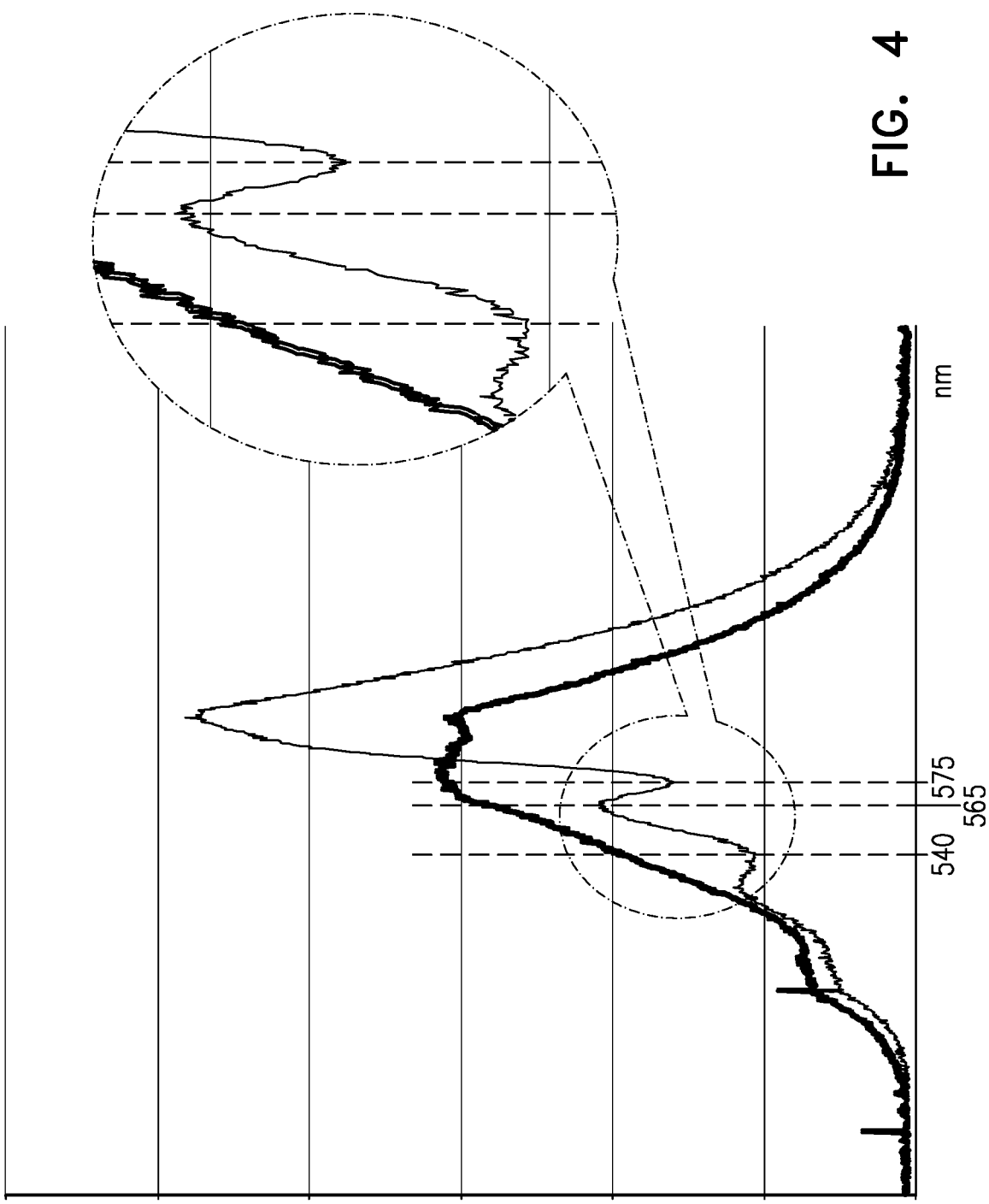
FIG. 4 is a graph showing spectrograms that were recorded from stool samples, in accordance with some applications of the present invention.

Reference is now made to FIG. 4, which is a graph showing spectrograms that were recorded from stool samples, in accordance with some applications of the present invention. A raw human stool sample and a human stool sample into which 0.2 ml of blood had been injected were placed inside a glass container (with dimensions 86×86×90 mm) that contained tap water to a height of about 70 mm (~500 cc of water). White LED light in the range of 400-700 nm and an intensity of approximately 220 lumens was directed into the container, and spectrograms of the light that was reflected from the container were acquired using a standard spectrometer.

The thicker curve is the spectrogram that was obtained from the raw stool sample, and the thinner curve is the spectrogram that was obtained from the stool with blood. As may be observed, in the enlarged portion of the graph, the spectrogram that was obtained from the sample that includes blood includes a characteristic trough-peak-trough shape at approximately 540 nm (trough), 565 nm (peak) and 575 nm (trough). This characteristic shape is an example of a blood signature, the shape being indicative of the presence of blood. Specifically, this shape indicates light absorption by oxyhemoglobin, which is present in erythrocytes in the blood.

The above results indicate that a blood signature can be detected within a stool sample under certain conditions. Furthermore, the above results were obtained by using a spectrogram which analyzes the overall spectral profile of the sample. If analyzing the sample on a pixel-by-pixel basis, as is the case in certain applications of the present invention, the blood signature can be expected to be detected with greater sensitivity and specificity.

Figure 5:
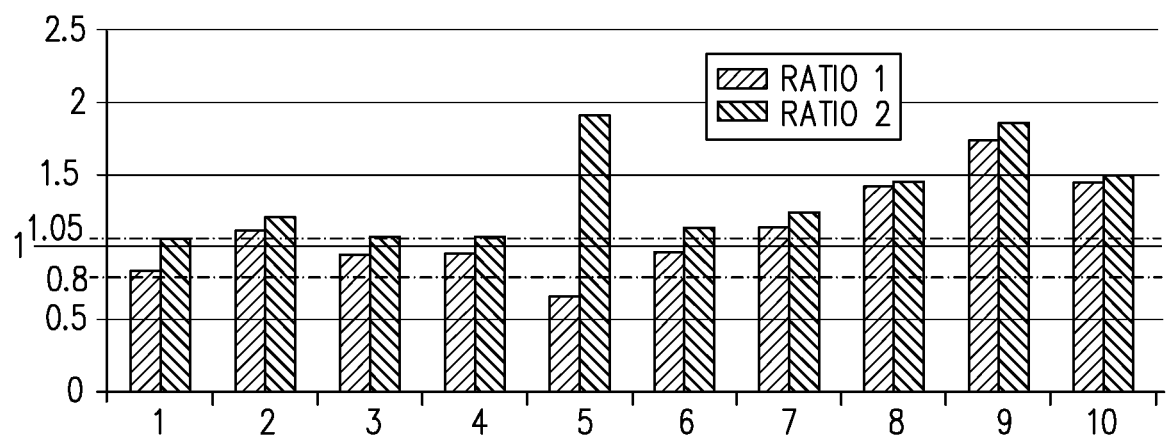
FIG. 5 is a bar-chart showing aspects of spectral components that were recorded from respective samples, during an experiment conducted in accordance with some applications of the present invention.

Reference is now made to FIG. 5, which is a bar-chart showing ratios of spectral components that were recorded from respective samples, during an experiment conducted in accordance with some applications of the present invention. Using the technique described above with respect to FIG. 4, the spectrograms of a plurality of sample were analyzed. The sample included:
 1. Fresh beet.
 2. Raw fresh meat.
 3. A fecal sample that did not contain blood.
 4. A second fecal sample that did not contain blood.
 5. A mixture of rum and red food colorant.
 6. A sample containing feces and 0.2 ml of blood, in which the sample was not mixed.

7. A sample containing feces and 0.2 ml of blood, in which the sample was mixed once by stirring with a rod.

8. A sample containing feces and 0.2 ml of blood, in which the sample was mixed twice by stirring with a rod.

9. A sample containing feces and 5 drops of blood, in which the sample was not mixed.

10. A sample containing feces and 5 drops of blood, in which the sample was mixed twice by stirring with a rod.

The blood was obtained from a blood bank and had been preserved in citrate.

For each of the samples, the received spectrogram was analyzed by calculating two ratios. Ratio 1 was the ratio of the intensity of a 10 nm band centered around 565 nm, to the intensity of a 10 nm band centered around 575 nm (I(565)/I(575)). Ratio 2 was the ratio of the intensity of a 10 nm band centered around 565 nm, to the intensity of a 10 nm band centered around 540 nm (I(565)/I(540)). For the purpose of the experiment, thresholds were set at 1.05 for ratio 1 and 0.8 for ratio 2, such that if ratio 1 would exceed 1.05 and ratio 2 would exceed 0.8, this would be an indication that the sample contains blood. This is because a sample that contains blood would be expected to have a blood signature with a characteristic trough-peak-trough shape at approximately 540 nm (trough), 565 nm (peak) and 575 nm (trough), whereas for a sample that does not contain blood, the slope of the spectrogram could be expected to increase between 540 nm and 575 nm, as shown in the thick curve of FIG. 4. The results are indicated in the bar-chart shown in FIG. 5 and are summarized in the table below:

| Sample | Contained human blood | Both ratios indicate that sample contains blood |
|---|---|---|
| 1 | No | No |
| 2 | No (but contained animal erythrocytes) | Yes |
| 3 | No | No |
| 4 | No | No |
| 5 | No | No |
| 6 | Yes | No |
| 7 | Yes | Yes |
| 8 | Yes | Yes |
| 9 | Yes | Yes |
| 10 | Yes | Yes |

As may be observed based on FIG. 5 and the above table, in general using the above-described ratios and thresholds, blood was detected in feces in four out of five cases. Using the above-described ratios and thresholds, in general, blood was not detected in cases in which blood had not been present in the sample, except for the meat sample (sample 2), which is discussed below. These results indicate that blood can be detected in a bodily emission by spectrally analyzing the emission, using techniques as described herein. Therefore, for some applications of the present invention, spectral bands that are centered around a wavelength that is in the range of 530 nm to 785 nm are detected. Typically, two or more spectral bands are detected that are centered around approximately 540 nm, 565 nm, and 575 nm. The widths of the spectral bands are typically greater than 3 nm (e.g., greater than 5 nm, or greater than 8 nm), and/or less than 40 nm (e.g., less than 20 nm, or less than 12 nm), e.g., between 3 and 40 nm, between 5 and 20 nm, or between 8 and 12 nm. For some applications, one or more ratios of the intensities of the aforementioned spectral bands with respect to one another are determined. For example, the ratio of the intensity of the spectral band that is centered around approximately 565 nm to that of the band centered around approximately 575 nm (or vice versa) may be determined, and/or the ratio of the intensity of the spectral band that is centered around approximately 565 nm to that of the band centered around approximately 540 nm (or vice versa) may be determined. For some applications, a different relationship between the intensities of the aforementioned spectral bands with respect to one another is determined. For some applications, a relationship between a parameter of the respective spectral bands other than intensity is determined.

It is noted that the results shown in FIG. 5 and summarized in the above table reflect a portion of the samples that were analyzed. In general, there were no false positives, except for when the meat sample was analyzed. This is to be expected, since raw fresh meat has residues of animal blood, which dissolves in the water. In accordance with some applications of the present invention, such false positives are reduced by asking the subject questions, such as whether the subject ate red meat within a given times interval of defecating, as described hereinabove.

False negatives were found when blood was injected into solid feces and did not reach the water (which was the case in sample 6). In accordance with some applications of the present invention, such false negatives are reduced by mixing, vibrating, and/or agitating feces inside the toilet bowl, in accordance with techniques described herein. It is noted that in the experiment, blood was mixed with the stool when the stool was disposed inside the glass container. Typically, when a person defecates into a toilet bowl, the feces is agitated by virtue of the feces falling into and impacting the toilet bowl. Therefore, for some applications of the present invention, no active agitation is provided to the feces disposed in the toilet bowl. In addition, there were false negatives (not shown in FIG. 5) in cases in which blood with beet was used as the sample. For some applications of the present invention, such false negatives are reduced by using greater light intensity than was used in the above-described experiment. It is further noted that since, in accordance with some applications, the analysis of bodily emissions is performed over a period of time, if hidden blood is missed in some emissions, it is likely to be detected in others.

Figure 6:
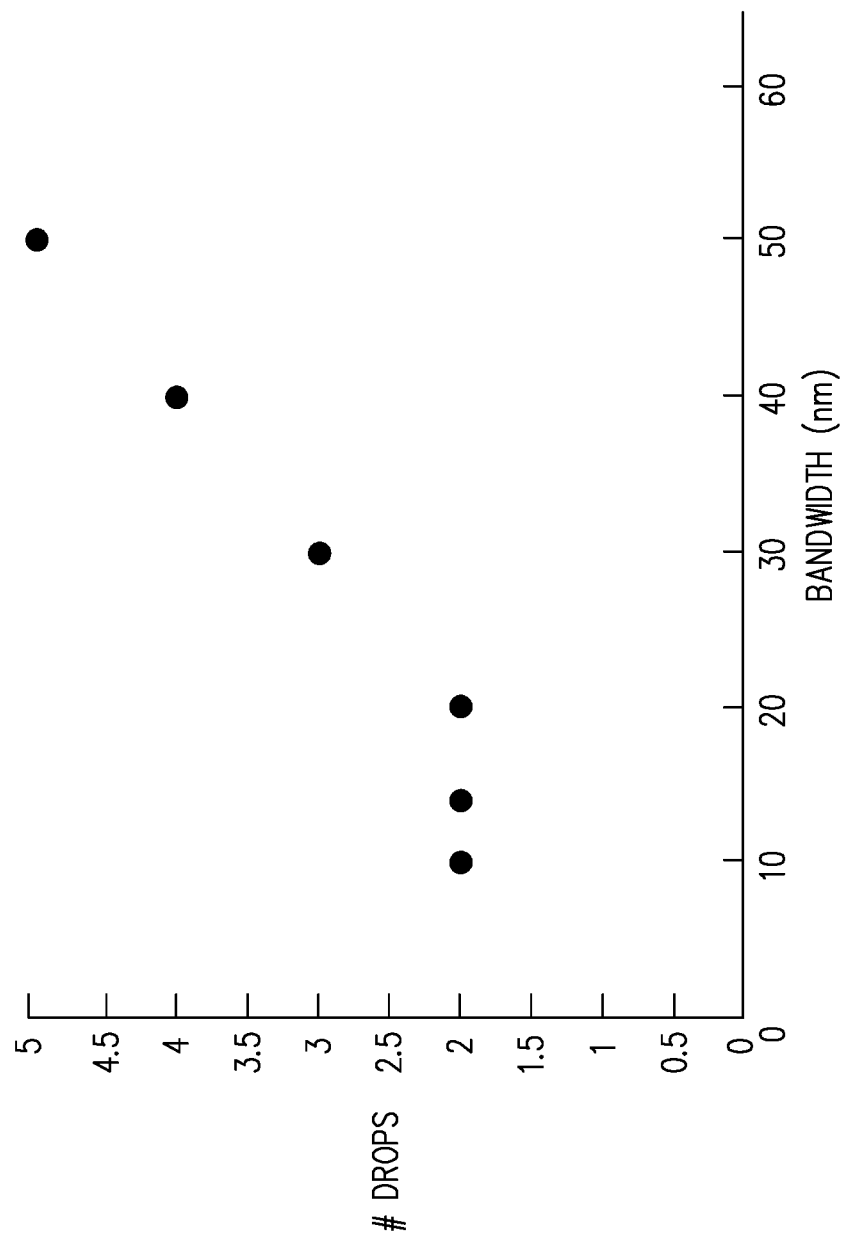
FIG. 6 is a graph showing the results of an experiment that was performed, in accordance with some applications of the present invention.

Reference is now made to FIG. 6, which is a graph showing the results of a simulation that was performed, in accordance with some applications of the present invention. Spectrograms of (a) feces and (b) five drops of blood obtained in an experiment as described hereinabove were used. The spectrogram of the five drops of blood was divided by five, to simulate the spectrogram of one drop, and to improve signal-to-noise ratio relative the spectrogram of a single drop of blood being used. A simulation was performed in order to artificially mix the spectra, such as to produce the effect of feces mixed with respective amount of blood. The above-described first and second ratios were then calculated for increasing bandwidths of spectral filter. FIG. 6 is a plot showing the minimum number of drops that was detectable for each bandwidth. It may be observed that up until a bandwidth of 20 nm, two drops of blood were detectable, whereas for bandwidths of 30 nm and more, a minimum of three drops of blood were required in order for the blood to be detectable. Therefore, for some applications of the present invention, two or more spectral bands are detected that are centered around approximately 540 nm, 565 nm, and 575 nm, and the widths of the spectral bands are typically greater than 3 nm (e.g., greater than 5 nm, or greater than 8 nm), and/or less than 40 nm (e.g., less than 20 nm, or less than 12 nm), e.g., between 3 and 40 nm, between 5 and 20 nm, or between 8 and 12 nm.

Figure 7:
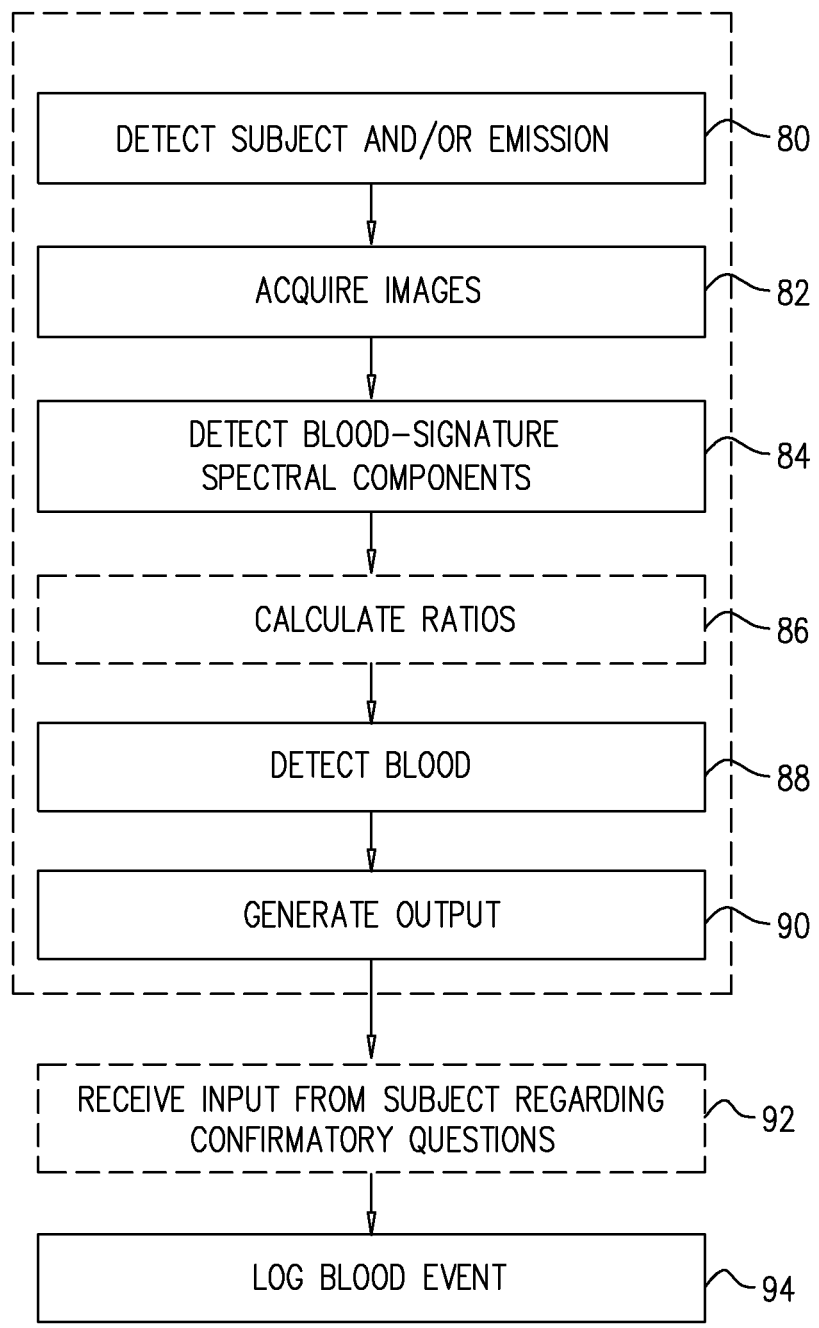
FIG. 7 is a flowchart showing steps that are performed, in accordance with some applications of the present invention.

Reference is now made to FIG. 7, which is a flowchart showing steps of a procedure that is performed, in accordance with some applications of the present invention.

In a first step (step 80), sensor module 22 (e.g., subject sensor 40 of the sensor module) detects a presence of the subject in a vicinity of or on the toilet, and/or detects that a bodily emission has been emitted into the toilet, as described hereinabove with reference to FIG. 2. In response thereto, imaging component 24 of the sensor module receives light from the toilet bowl, typically by acquiring images using one or more cameras (e.g., one or more multispectral cameras, or one or more hyperspectral cameras) (step 82). As noted hereinabove, the scope of the present invention includes receiving radiation at any spectral band, and is not limited to receiving radiation in the visible light range.

The received light is analyzed (e.g. spectrally analyzed) by a computer processor, which may be computer processor 44 of the sensor module, or a different computer processor, as described hereinabove. Typically, spectral bands are detected that centered around a wavelength that is in the range of 530 nm to 785 nm. Further typically, blood-signature spectral components are detected (step 84). For example, one or more spectral components within the received light that are indicative of light absorption by a component of erythrocytes (e.g., oxyhemoglobin) may be detected. As described hereinabove, for some applications of the present invention, two or more spectral bands are detected that are centered around approximately 540 nm, 565 nm, and 575 nm. (As noted hereinabove, a spectral band that is described herein as being centered around approximately a given spectral value should be interpreted as including a spectral band centered around the given value plus/minus 5 nm.) For some applications, the detected spectral components are analyzed by calculating ratios of the intensities of respective components with respect to one another (step 86), for example, as described hereinabove. Alternatively or additionally, the spectral components may be analyzed in a different manner (Step 86 is inside a dashed box to indicate that the specific step of calculating ratios is optional.) In response to the spectral analysis, the computer processor detects blood (step 88) and generates an output (step 90), for example, on user interface device 32.

The scope of the present invention includes detecting any spectral components that are indicative of light absorption by a component of erythrocytes, for example spectral components that are indicative of hemoglobin methemoglobin, and/or heme. For some application spectral components that are indicative of light absorption of urine and/or feces are detected. For some applications, the computer processor determines whether there is feces and/or urine together with blood, in order to confirm that detected blood is blood that is associated with feces and/or urine and is not from a different source. In addition, the scope of the present invention includes determining any type of relationship between parameters (e.g., intensities) of respective spectral bands within the received light and is not limited to determining ratios between the parameters (e.g., intensities) of the respective spectral bands. Furthermore, even for applications in which ratios 1 and 2 as described hereinabove are calculated, the thresholds that are described as having been used are illustrative, and the scope of the present invention includes using different thresholds to those described hereinabove. For example, for applications in which calibrated light sensors are used, a threshold of more than 1 and/or less than 1.5 (e.g., between 1 and 1.5) may be used for ratio 1 (i.e., I(565)/I(575)), and a threshold of more than 0.7 and/or less than 1 (e.g., between 0.7 and 1) may be used for ratio 2 (i.e., I(565)/I(540)). For applications in which the light sensors are uncalibrated, the ratios may be different.

It is noted that, at this stage, the output may indicate a suspicion of the subject's blood being in the bodily emission. For some applications, in order to confirm the suspicion, the user is requested to provide an input by the user being asked confirmatory questions (the answers to which are typically indicative of the source of the detected blood), as described hereinabove. The computer processor receives the input from the subject regarding the confirmatory questions (step 92). If the input from the user indicates that the detection of blood was not a false positive (that may have been caused, for example, by the subject having eaten red meat), then the computer processor logs that a blood event has occurred (step 94). For example, the computer processor may log the event on memory 46 of the sensor module. For some applications, the blood event is logged even without receiving an input from the user (step 92). For example, the computer processor may account for false positives in a different manner, such as by incorporating a likelihood of false positives into a threshold that is used to monitor blood events over a long term period. (Step 92 is inside a dashed box to indicate that this step is optional.)

Typically, steps 80-90 of FIG. 7 (the steps inside the large, dashed box) are performed without requiring any action by the subject or any other person, subsequent to the subject emitting a bodily emission into the toilet bowl.

Applications of the invention described herein can take the form of a computer program product accessible from a computer-usable or computer-readable medium (e.g., a non-transitory computer-readable medium) providing program code for use by or in connection with a computer or any instruction execution system, such as computer processor 44, or a computer processor of user interface device 32. For the purpose of this description, a computer-usable or computer readable medium can be any apparatus that can comprise, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Typically, the computer-usable or computer readable medium is a non-transitory computer-usable or computer readable medium.

Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD. For some applications, cloud storage is used.

A data processing system suitable for storing and/or executing program code will include at least one processor (e.g., computer processor 44, or a computer processor of user interface device 32) coupled directly or indirectly to memory elements (e.g., memory 46, or a memory of user interface device 32) through a system bus. The memory elements can include local memory employed during actual execution of the program code, bulk storage, and cache memories which provide temporary storage of at least some program code in order to reduce the number of times code must be retrieved from bulk storage during execution. The system can read the inventive instructions on the program storage devices and follow these instructions to execute the methodology of the embodiments of the invention.

Network adapters may be coupled to the processor to enable the processor to become coupled to other processors or remote printers or storage devices through intervening private or public networks. Modems, cable modem and Ethernet cards are just a few of the currently available types of network adapters.

Computer program code for carrying out operations of the present invention may be written in any combination of one or more programming languages, including an object oriented programming language such as Java, Smalltalk, C++ or the like and conventional procedural programming languages, such as the C programming language or similar programming languages.

It will be understood that blocks of the flowchart shown in FIG. 7 and combinations of blocks in the flowchart, can be implemented by computer program instructions. These computer program instructions may be provided to a processor of a general purpose computer, special purpose computer, or other programmable data processing apparatus to produce a machine, such that the instructions, which execute via the processor of the computer (e.g., computer processor 44, or a computer processor of user interface device 32) or other programmable data processing apparatus, create means for implementing the functions/acts specified in the flowchart and/or algorithms described in the present application. These computer program instructions may also be stored in a computer-readable medium (e.g., a non-transitory computer-readable medium) that can direct a computer or other programmable data processing apparatus to function in a particular manner, such that the instructions stored in the computer-readable medium produce an article of manufacture including instruction means which implement the function/act specified in the flowchart blocks and algorithms. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or algorithms described in the present application.

Computer processor 44 and the other computer processors described herein are typically hardware devices programmed with computer program instructions to produce a special purpose computer. For example, when programmed to perform the algorithms described with reference to FIG. 7, the computer processor typically acts as a special purpose bodily-emission-analysis computer processor. Typically, the operations described herein that are performed by computer processors transform the physical state of a memory, which is a real physical article, to have a different magnetic polarity, electrical charge, or the like depending on the technology of the memory that is used.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for use with a bodily emission of a subject that is disposed within a toilet bowl, the method comprising: while the bodily emission is disposed within the toilet bowl, receiving light from the toilet bowl using one or more light sensors;
using a computer processor:
determining intensities of at least three spectral bands within the received light that are within a range of 530 nm to 785 nm, by analyzing the received light;
based upon the determined intensities of the at least three spectral bands, determining that there is a presence of blood within the bodily emission; and
generating an output on an output device, at least partially in response thereto.

2. The method according to claim 1, wherein the bodily emission includes feces, and wherein determining that there is a presence of blood within the bodily emission comprises determining that there is a presence of blood within the feces.

3. The method according to claim 1, wherein the bodily emission includes urine, and wherein determining that there is a presence of blood within the bodily emission comprises determining that there is a presence of blood within the urine.

4. The method according to claim 1, wherein receiving light from the toilet bowl using one or more light sensors comprises receiving one or more images from the toilet bowl using one or more cameras, and wherein analyzing the received light comprises analyzing a plurality of respective pixels within the one or more images on an individual basis.

5. The method according to claim 1, wherein receiving light from the toilet bowl using one or more light sensors comprises, subsequent to the subject emitting the bodily emission into the toilet bowl, while the bodily emission is at least partially disposed within water of the toilet bowl, receiving the light from the toilet bowl using one or more light sensors, without requiring any action to be performed by any person subsequent to the emission.

6. The method according to claim 1, wherein determining intensities of at least three spectral bands within the received light that are within the range of 530 nm to 785 nm comprises determining intensities of at least two spectral bands within the received light that are centered around approximate wavelengths selected from the group consisting of: 540 nm, 565 nm, and 575 nm.

7. The method according to claim 1, further comprising determining a ratio of the intensities of at least two of the spectral bands within the received light, wherein determining that there is a presence of blood within the bodily emission comprises determining that there is a presence of blood within the bodily emission in response to the ratio of the intensities of at least two of the spectral bands within the received light.

8. Apparatus for use with a bodily emission of a subject that is disposed within a toilet bowl, and an output device, the apparatus comprising:
one or more light sensors that are configured to receive light from the toilet bowl, while the bodily emission is disposed within the toilet bowl; and
a computer processor configured to:
determine intensities of at least three spectral bands within the received light that are within a range of 530 nm to 785 nm, by analyzing the received light;
based upon the determined intensities of the at least three spectral bands, determine that there is a presence of blood within the bodily emission; and
generate an output on the output device, at least partially in response thereto.

9. The apparatus according to claim 8, wherein the bodily emission includes feces, and wherein the computer processor is configured to determine that there is a presence of blood within the bodily emission by determining that there is a presence of blood within the feces.

10. The apparatus according to claim 8, wherein the bodily emission includes urine, and wherein the computer processor is configured to determine that there is a presence of blood within the bodily emission by determining that there is a presence of blood within the urine.

11. The apparatus according to claim 8, wherein the one or more light sensors comprise one or more cameras configured to acquire one or more images of the bodily emission, and wherein the computer processor is configured to analyze the received light by analyzing a plurality of respective pixels within the one or more images on an individual basis.

12. The apparatus according to claim 8, wherein, subsequent to the subject emitting the bodily emission into the toilet bowl, while the bodily emission is at least partially disposed within water of the toilet bowl, the one or more light sensors are configured to receive the light from the toilet bowl, without requiring any action to be performed by any person subsequent to the emission.

13. The apparatus according to claim 8, wherein the computer processor is configured to determining intensities of at least three spectral bands within the received light that are within the range of 530 nm to 785 nm by determining intensities of at least two spectral bands within the received light that are centered around approximate wavelengths selected from the group consisting of: 540 nm, 565 nm, and 575 nm.

14. The apparatus according to claim 8, wherein the computer processor is configured to:
determine a ratio of the intensities of at least two of the spectral bands within the received light; and
determine that there is a presence of blood within the bodily emission in response to the ratio of the intensities of at least two of the spectral bands within the received light.

15. A method for use with a bodily emission of a subject that is disposed within a toilet bowl, the method comprising:
while the bodily emission is disposed within the toilet bowl, receiving light from the toilet bowl using one or more light sensors;
using a computer processor:
determining intensities of one or more spectral bands within the received light that are indicative of light absorption by a component of erythrocytes, by analyzing the received light;
in response thereto, determining that there is a presence of blood within the bodily emission; and
at least partially in response thereto, requesting an input from the subject that is indicative of a cause of the presence of the blood.

16. The method according to claim 15, wherein requesting the input from the subject that is indicative of a cause of the presence of the blood comprises requesting an input from the subject indicating food that the subject has eaten.

17. The method according to claim 15, wherein requesting the input from the subject that is indicative of a cause of the presence of the blood comprises requesting an input from the subject indicating medication that the subject has taken.

* * * * *